United States Patent
Porter et al.

(12) 
(10) Patent No.: US 6,233,530 B1
(45) Date of Patent: May 15, 2001

(54) CONTROL SYSTEM FOR A FAILURE MODE TESTING SYSTEM

(75) Inventors: Alexander J. Porter, Kalamazoo; Mark Allen Smith, Shelbyville, both of MI (US)

(73) Assignee: Entela, Inc., Grand Rapids, MI (US)

( * ) Notice: Subject to any disclaimer, the term of this patent is extended or adjusted under 35 U.S.C. 154(b) by 0 days.

(21) Appl. No.: 09/427,456

(22) Filed: Oct. 26, 1999

Related U.S. Application Data

(63) Continuation-in-part of application No. 09/316,574, filed on May 21, 1999, which is a continuation-in-part of application No. 08/929,839, filed on Sep. 15, 1997.

(51) Int. Cl.$^7$ ........................................................ G01M 7/06
(52) U.S. Cl. ................................................. 702/77; 73/663
(58) Field of Search .......................... 702/77, 76; 73/5.7, 73/649, 663, 12.01, 571, 577, 664, 662; 324/76.21, 76.19; 708/823

(56) References Cited

U.S. PATENT DOCUMENTS

| | | | |
|---|---|---|---|
| 4,181,026 | * 1/1980 | Abstein et al. | 73/665 |
| 4,445,381 | * 5/1984 | Russenbeger | 73/666 |
| 5,079,955 | * 1/1992 | Eberhardt | 73/799 |
| 5,305,645 | * 4/1994 | Reifsnider et al. | 73/808 |
| 5,315,882 | * 5/1994 | Meyer et al. | 73/862.044 |
| 5,425,276 | * 6/1995 | Gram et al. | 73/816 |
| 5,476,009 | * 12/1995 | Dimarogonas | 73/582 |
| 5,487,301 | * 1/1996 | Muler et al. | 73/118.1 |
| 5,665,919 | * 9/1997 | Woyski et al. | 73/665 |
| 5,752,834 | * 5/1998 | Ling | 434/58 |

\* cited by examiner

*Primary Examiner*—Marc S. Hoff
*Assistant Examiner*—Edward Raymond
(74) *Attorney, Agent, or Firm*—Harness, Dickey & Pierce, P.L.C.

(57) ABSTRACT

A control system for a failure mode testing system is described. The control system employs at least one control algorithm that enables the testing system to be operated at optimal pressure and frequency levels in order to generate a desired system response, such as a desired energy level and desired slope of the fast Fourier transform of the system response. Also described are a pressure dither system and a frequency ringing system for enhancing the operation of the actuator cylinders of the failure mode testing system. All three of the systems can be incorporated, either singularly or in combination, into a computer software program that can be employed to operate and control the failure mode testing system.

70 Claims, 4 Drawing Sheets

CONTROL SYSTEM FOR A FAILURE MODE TESTING SYSTEM

CROSS-REFERENCE TO RELATED APPLICATIONS

This application is a continuation-in-part application of U.S. patent application Ser. No. 09/316,574 entitled "Design Maturity Algorithm", filed May 21, 1999, pending, which is a continuation-in-part application of U.S. patent application Ser. No. 08/929,839 entitled "Method and Apparatus For Optimizing the Design of Products", filed Sep. 15, 1997, pending, the entire specifications of which are expressly incorporated herein by reference.

FIELD OF THE INVENTION

The present invention relates to a new and improved control system for a failure mode testing system. The control systems employs at least one control algorithm in order to optimize the performance of the failure mode testing system.

BACKGROUND OF THE INVENTION

The recent advent of failure mode testing systems to activate failure modes has enabled manufacturers to discover latent defects or flaws which may eventually lead to the failure of a product, component or sub-component. The methodology of these testing systems generally involves the application of one or more types and/or levels of stimuli to the product, component or sub-component until one or more failure modes are activated. Typically, one of the stimuli includes vibration, such as that caused by striking a piston, rod, or other suitable device, against the product, component or sub-component itself, or a surface in contact with the product, component or sub-component. When the failure mode is activated, the failed product, component or sub-component is then either repaired, replaced, or redesigned. This process may then be repeated in order to activate and eliminate other failure modes.

A proprietary testing system has been developed by Entela, Inc. (Grand Rapids, Mich.) and is referred to as a failure mode verification testing system. This system, which is described in commonly-owned, co-pending U.S. patent application Ser. No. 09/316,574 entitled "Design Maturity Algorithm", filed May 21, 1999, and U.S. patent application Ser. No. 08/929,839 entitled "Method and Apparatus For Optimizing the Design of Products", filed Sep. 15, 1997, employs an apparatus which is capable of generating a wide variety of stress patterns, especially six axis uniform random stress patterns, in a product, component, or sub-component in order to activate the failure modes of that particular product, component, or sub-component.

A six axis uniform random stress is generally defined as the stress history at a point having uniform random distribution with the stress being comprised of tension and compression stress in three orthogonal axes and torsion stress about the same three orthogonal axes. Six axis uniform random stress patterns are generally defined as six axis uniform random stress at all points on a product such that the stress history of the six axis uniform random stress at each point forms a time history of non-repeating stress patterns.

The apparatus uses six axis uniform random actuation at one or more mounting locations of a product to produce six axis uniform random stress patterns in the product. These six axis uniform random stress patterns identify failure modes previously uncovered with other testing methodologies. Furthermore, the simultaneous introduction of other stimuli (at varying levels), such as temperature, vibration, pressure, ultraviolet radiation, chemical exposure, humidity, mechanical cycling, and mechanical loading, identify other failure modes associated with the product.

In order to create the six axis uniform random stress patterns in the product, the apparatus employs a plurality (preferably six) of actuators, also referred to as force imparting members, that can be operated either pneumatically, hydraulically, by a combination of both pneumatic and hydraulic power, or any other force imparting mechanism. A portion of the actuators, such as the cylinders, are typically mounted (including slidingly), either directly or indirectly, onto one or more support members.

If six actuators are being used, they are preferably arranged in pairs, each pair being set about 120 degrees apart from the other pair. Each actuator is simply comprised of a cylinder acting in cooperation with a piston in order to produce force and torque upon a point of rotation. The pressure to each actuator is preferably cycled between maximum extend pressure and maximum retract pressure in a linear "saw-tooth" manner. The frequency for each actuator is slightly different. This difference in frequency causes an interference pattern of the cycling as the actuators come in and out of phase with each other. It is this difference in the frequencies of the actuators which creates a six axis uniform random stress in the product. By way of a non-limiting example, the six pneumatic actuators can be operated at frequencies of 1.8 Hz, 1.9 Hz, 2.0 Hz, 2.1 Hz, 2.2 Hz, 2.3 Hz, and 2.4 Hz, respectively. Therefore, as the actuators come in and out of phase with one another, the frequency content in the center will go from about 2 Hz to infinity. It should be noted that other frequencies may be used for the individual actuators in order to produce an even lower frequency.

A portion of the actuators, such as the pistons, are typically connected, either directly or indirectly, to a platform, such as a hub, upon which the product is mounted. As the actuators are actuated, they produce a force which generates a torque about a point of rotation on the platform. It should be noted that whether a torque is generated about the point of rotation will depend upon which actuators are being actuated and in what sequence with respect to one another. The force and torque are eventually transferred from the platform to the product itself, thus creating the six axis uniform random stress patterns in the product.

During routine operation of the apparatus, it is not uncommon for the actuators to be cycled back and forth very rapidly. Therefore, it is impractical to manually attempt to continuously adjust the various operational parameters that affect actuator operation, such as the pressure and frequency of the cylinders. The pressure parameter concerns the amount of pressure in the air line (e.g., in a pneumatic system) in communication with the cylinder of the actuator, which is typically expressed in pounds per square inch (psi). The frequency parameter concerns the frequency that each cylinder is set to, which is typically expressed in Hertz (Hz).

By way of a non-limiting example, the system response of the apparatus can be measured in terms of energy E (e.g., grms or peak G) and slope m of the fast Fourier transform (FFT) of the system response. A FFT is typically performed on a time history or a response. By way of a non-limiting example, an acceleration signal from an accelerometer would provide a varying signal in time. The FFT of the acceleration signal would give the acceleration level vs. frequency. From the FFT of the acceleration signal, the slope of the FFT plot (i.e., response level vs. frequency) can be determined.

Preferably, a desired energy level E having a desired slope m (e.g., flat) is produced by the application of appropriate levels of pressure and frequency. For example, if the energy level were plotted on the Y-axis of a graph and the frequency level were plotted on the X-axis of that same graph, the majority of data points could be bisected by a line having a slope substantially equal to zero. Thus, the energy level would be substantially constant over the entire frequency range.

Due to the large number of calculations that would have to be performed on a split second basis for each of the six actuators, it is impractical to manually perform the calculations, let alone make the requisite adjustments to the operational parameters of the actuators, without adversely affecting the efficient performance of the testing system. Nonetheless, it is important to the optimal operation of the testing system that the desired performance parameters are achieved and maintained during the course of the testing procedure.

Additionally, with respect to pressure, it has been observed that by keeping each cylinder at a constant pressure, the actuators have a tendency, due to frictional forces and historesis, to gravitate towards a set point and get stuck, thus causing the actuators to improperly function. For example, if the pressure is slightly too high, the apparatus will tend to drift up and then get stuck. Conversely, if the pressure is slightly too low, the apparatus will tend to drift down and then get stuck.

Furthermore, with respect to frequency, it has been observed that by keeping each cylinder at a specific individual frequency, over time one of the actuators will receive less energy than the other actuators. For example, if one cylinder of an actuator pair is operated at 5 Hz at a given pressure, and the other cylinder of the actuator pair is operated at 5.5 at that same given pressure, then over time a little more energy is being given to one cylinder than the other. The fact that one cylinder receives more energy can be confirmed by calculating the integration of the given pressure at the slightly higher frequency. As a result, the apparatus will tend to drift toward the actuator having the lowest energy level, thus causing performance problems.

Therefore, there exists a need for a control system for determining if the desired system response of a failure mode testing system is or is not present. The control system should be capable of quickly, accurately, and if needed, constantly adjusting the operational parameters (e.g., pressure and frequency) until the desired system response is achieved and subsequently maintained.

SUMMARY OF THE INVENTION

General objects of the present invention are to facilitate and enhance testing of products under various conditions, to provide more comprehensive testing and to make testing more efficient by reducing the energy, time, and expense required to undertake testing.

Another object of the present invention is to provide a new and improved control system for a failure mode testing system.

Still another object of the present invention is to provide a new and improved control algorithm for a failure mode testing system.

In accordance with one embodiment of the present invention, a control system for a failure mode testing system having a determinable system response is provided, wherein the testing system includes a plurality of actuator cylinders, each cylinder operating at an initial pressure and an initial frequency, wherein the frequency of each of the cylinders is different, comprising:

a) selecting a desired system response;
b) determining the system response;
c) determining whether the desired system response is present; and
d) changing an operational parameter of the cylinders by a sufficient amount in order to achieve the desired system response, wherein the operational parameter is selected from the group consisting of pressure, frequency, and combinations thereof.

A more complete appreciation of the present invention and its scope can be obtained from understanding the accompanying drawings, which are briefly summarized below, the followed detailed description of the invention, and the appended claims.

BRIEF DESCRIPTION OF THE DRAWINGS

The same reference numerals refer to the same parts throughout the various Figures.

DETAILED DESCRIPTION OF THE INVENTION

In accordance with one embodiment of the present invention, a control system employing at least one control algorithm is provided for use in conjunction with a failure mode testing system. The control algorithm enables the testing system to be operated at optimal pressure and frequency levels in order to generate a desired system response. The control algorithm can be incorporated into a computer software program that can be employed to control and operate the failure mode testing system (e.g., a control system).

The control algorithm of the present invention is actually comprised of a number of discrete algorithms, each of which generally determine a single piece of information, based on data provided by various input sources, such as sensors, detectors, data storage mediums, and so forth.

By way of a non-limiting example, one set of algorithms determines the change in energy due to pressure, the change in energy due to frequency, the change in slope due to pressure, and the change in slope due to frequency. That information is then utilized by additional algorithms to determine the average energy and slope of the system response. That information is then utilized by still additional algorithms to determine the new target energy and slope of the system response. Finally, that information is utilized by still yet another set of algorithms to determine the new target frequency and pressure to achieve the new target energy and slope of the system response.

Figure 1:
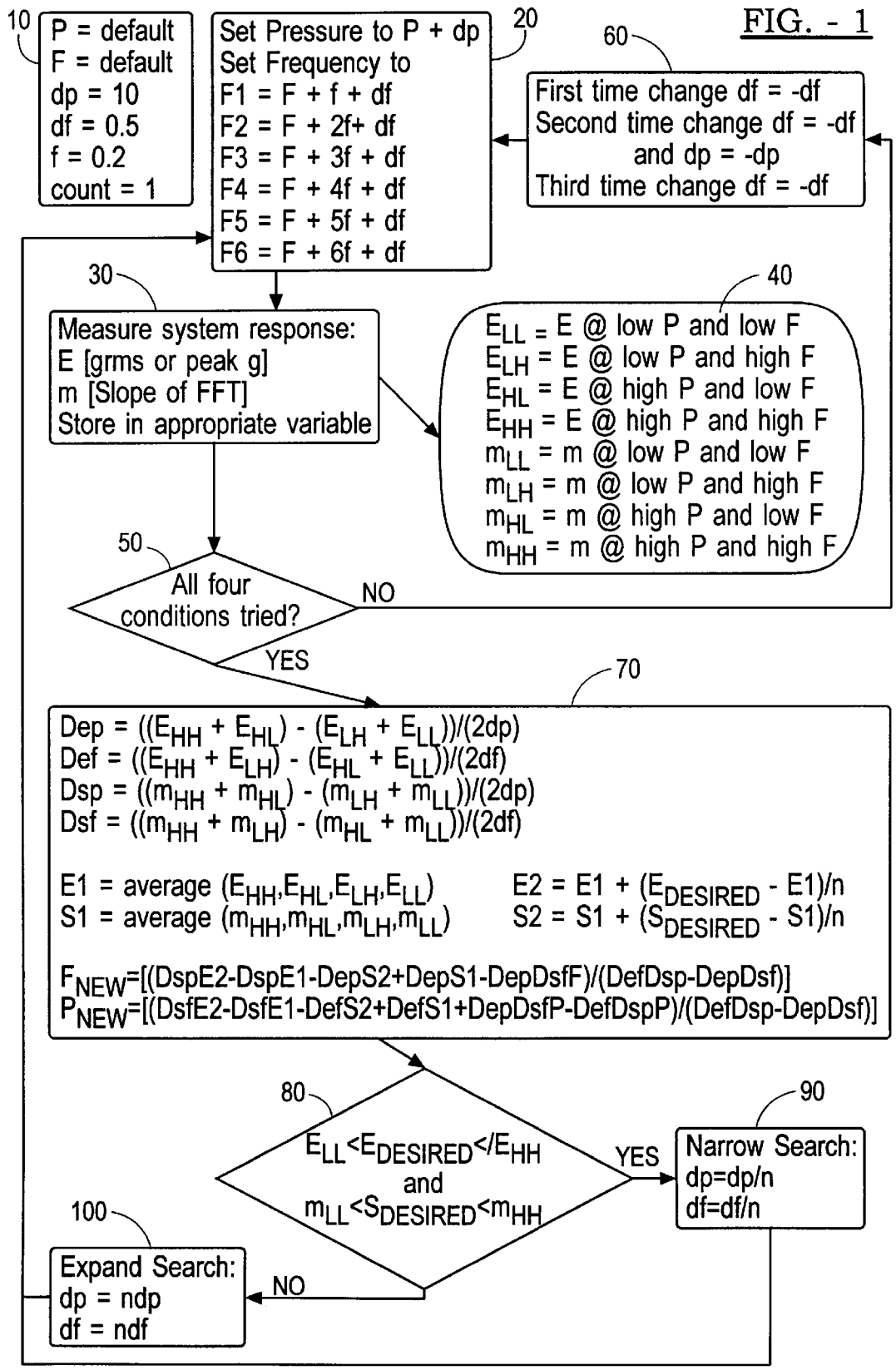
FIG. 1 is a schematic of a control system for a failure mode testing system, in accordance with one aspect of the present invention.

With reference to FIG. 1, there is illustrated a schematic view of a non-limiting example of a control system employing at least one control algorithm, in accordance with one embodiment of the present invention. The control algorithm is intended to be used in conjunction with a failure mode testing system employing an apparatus that is capable of producing six axis uniform random stress patterns in a product.

As shown in condition box 10, and by way of a non-limiting example, the actuators of the apparatus are assigned a pre-selected default pressure (P) and a pre-selected default frequency (F). These pre-selected defaults are set by the operator, and, of course, it should be noted that they may be changed or altered to meet the desired operational parameters of the testing system. Additionally, the pressure change (dp) is set at 10 psi (although any other figure may be substituted therefor), the frequency change (df) is set at 0.5 Hz (although any other figure may be substituted therefor), and the step frequency (f) is set at 0.2 Hz (although any other figure may be substituted therefor).

As shown in box 20, and by way of a non-limiting example, the pressure of the actuator cylinder is set to P+dp. Each of the actuator cylinders are set to different frequencies, F1, F2, F3, F4, F5, and F6, respectively. F1 is equal to F+f+df. The step frequency (f) is used to "step" the base frequency up to six distinct frequencies, i.e. a different frequency for each cylinder, as will become apparent from the following description. F2 is equal to F+2f+df, F3 is equal to F+3f+df, F4 is equal to F+4f+df, F5 is equal to F+5f+df, and F6 is equal to F+6f+df. Thus, all six of the actuator cylinders have a different frequency.

At this point, the testing system is permitted to operate, in that the actuators are actuated. As shown in box 30, and by way of a non-limiting example, the system response (e.g., of the cylinders) is measured, calculated, or otherwise determined, specifically the energy level (E) expressed in rms, peak G, or any other appropriate unit, and the slope m, expressed as the slope of the fast Fourier transform of the system response (i.e., time history which is the slope of the energy vs. the frequency plot).

This information is then stored in a data storage medium and/or device (e.g., RAM, hard drive, floppy disk, CD-ROM, or the like) as an appropriate variable, under four different conditions, i.e., high pressure/high frequency (HH), high pressure/low frequency (HL), low pressure/high frequency (LH), and low pressure/low frequency (LL).

As shown in box 40, and by way of a non-limiting example, the system response information generated is stored as eight different variables, i.e., $E_{LL}$ (measured E when both P and F are low), $E_{LH}$ (measured E when P is low and F is high), $E_{HL}$ (measured E when P is high and F is low), $E_{HH}$ (measured E when both P and F are high), $m_{LL}$ (measured m when both P and F are low, $m_{LH}$ (measured m when P is low and F is high), $m_{HL}$ (measured M when P is high and F is low), and $m_{HH}$ (measured m when both P and F are high).

At this point, decision node 50 is encountered which queries whether all four conditions have been tried (i.e., high/high, high/low, low/high, and low/low).

If all four conditions have not been tried, the control system prompts a change in either the pressure, frequency, and/or both, of the individual actuators, so that all four conditions are tried. As shown in Box 60, and by way of a non-limiting example, assuming that the first condition was low frequency/low pressure, then the first time change requires a high frequency/low pressure condition, the second time change requires a high frequency/high pressure condition, and the third time change requires a low frequency/high pressure condition. It should be noted that the sequence of these conditions may in any desired order. The critical consideration is that all four conditions have been tried, not the order in which they are tried. The method of changing the pressure and/or frequency is by adding or removing appropriate levels of pressure (i.e., ±dp) and/or frequency (i.e., ±df).

To illustrate this concept, consider the following non-limiting example. Assume that the default P is 30 psi, and the dp is 10 psi. Therefore, the initial pressure is set at 40 psi (i.e., P (30 psi)+dp (10 psi)=40 psi), which represents the "high" pressure condition (i.e., "plus" dp). Now, assume that the default frequency is 2 Hz, the step frequency is 0.2 Hz, and the df is 0.5 Hz. Therefore, the frequency of the first cylinder (F1) is 2.7 Hz (i.e., F (2 Hz)+f (0.2 Hz)+df (0.5 Hz)=2.7 Hz), the second cylinder (F2) is 2.9 Hz (i.e., F (2 Hz)+2f (0.4 Hz)+df (0.5 Hz)=2.9 Hz), the third cylinder (F3) is 3.1 Hz (i.e., F (2 Hz)+3f (0.6 Hz)+df (0.5 Hz)=3.1 Hz), the fourth cylinder (F4) is 3.3 Hz (i.e., F (2 Hz)+4f (0.8 Hz)+df (0.5 Hz)=3.3 Hz), the fifth cylinder (F5) is 3.5 Hz (i.e., F (2 Hz)+5f (1.0 Hz)+df (0.5 Hz)=3.5 Hz), and the sixth cylinder (F6) is 3.7 Hz (i.e., F (2 Hz)+6f (1.2 Hz)+df (0.5 Hz)=3.7 Hz), all of which represent the "high" frequency condition (i.e., "plus" df)

The apparatus is now operated under this particular high pressure/high frequency condition, the system response is measured (Box 30), and the energy/slope variables are calculated and stored (Box 40), and then decision node 50 is encountered. As only one condition has been tried (i.e., high pressure/high frequency), the control system will prompt the apparatus to try the three remaining conditions (i.e., high pressure/low frequency, low pressure/low frequency, and low pressure/high frequency).

With respect to the high pressure/low frequency condition, instead of adding the df Hz amount to each of the individual frequencies of the actuators, it is removed or subtracted. Therefore, the frequency of the first cylinder (F1) is 1.7 Hz (i.e., F (2 Hz)+f (0.2 Hz)+df (−0.5 Hz)=1.7 Hz), the second cylinder (F2) is 1.9 Hz (i.e., F (2 Hz)+2f (0.4 Hz)+df (−0.5 Hz)=1.9 Hz), the third cylinder (F3) is 3.1 Hz (i.e., F (2 Hz)+3f (0.6 Hz)+df (−0.5 Hz)=2.1 Hz), the fourth cylinder (F4) is 2.3 Hz (i.e., F (2 Hz)+4f (0.8 Hz)+df (−0.5 Hz)=2.3 Hz), the fifth cylinder (F5) is 2.5 Hz (i.e., F (2 Hz)+5f (1.0 Hz)+df (−0.5 Hz)=2.5 Hz), and the sixth cylinder (F6) is 2.7 Hz (i.e., F (2 Hz)+6f (1.2 Hz)+df (−0.5 Hz)=2.7 Hz), all of which represent the "low" frequency condition (i.e., "minus" df).

The apparatus is now operated under this particular high pressure/low frequency condition, the system response is measured (Box 30), and the energy/slope variables are calculated and stored (Box 40), and then decision node 50 is again encountered. As only two conditions have been tried (i.e., high pressure/high frequency, high pressure/low frequency), the control system will prompt the apparatus to try the two remaining conditions (i.e., low pressure/low frequency and low pressure/high frequency).

With respect to the low pressure/low frequency condition, the frequencies remain in the "low" condition; however, instead of adding the dp psi amount to the pressure of the actuators, it is removed or subtracted. Therefore, the pressure of all the cylinders is 20 psi (i.e., P (30 psi)−dp (10 psi)=20 psi), which represents the "low" pressure condition (i.e., "minus" dp).

The apparatus is now operated under this particular low pressure/low frequency condition, the system response is measured (Box 30), and the energy/slope variables are calculated and stored (Box 40), and then decision node 50 is again encountered. As only three conditions have been tried (i.e., high pressure/high frequency, high pressure/low frequency, low pressure/low frequency), the control system will prompt the apparatus to try the last remaining condition (i.e., and low pressure/high frequency).

With respect to the low pressure/high frequency condition, the pressure remains in the "low" condition; however, instead of subtracting the df Hz amount to the frequencies of each of the actuators, it is added. Therefore, the frequency of the first cylinder (F1) is 2.7 Hz (i.e., F (2 Hz)+f (0.2 Hz)+df (0.5 Hz)=2.7 Hz), the second cylinder (F2) is 2.9 Hz (i.e., F (2 Hz)+2f (0.4 Hz)+df (0.5 Hz)=2.9 Hz), the third cylinder (F3) is 3.1 Hz (i.e., F (2 Hz)+3f (0.6 Hz)+df (0.5 Hz)=3.1 Hz), the fourth cylinder (F4) is 3.3 Hz (i.e., F (2 Hz)+4f (0.8 Hz)+df (0.5 Hz)=3.3 Hz), the fifth cylinder (F5) is 3.5 Hz (i.e., F (2 Hz)+5f (1.0 Hz)+df (0.5 Hz)=3.5 Hz), and the sixth cylinder (F6) is 3.7 Hz (i.e., F (2 Hz)+6f (1.2 Hz)+df (0.5 Hz)=3.7 Hz), all of which represent the "high" frequency condition (i.e., "plus" df)

The apparatus is now operated under this particular low pressure/high frequency condition, the system response is measured (Box 30), and the energy/slope variables are calculated and stored (Box 40), and then decision node 50 is again encountered. As all four conditions have now been tried (i.e., high pressure/high frequency, high pressure/low frequency, low pressure/low frequency, and low pressure/high frequency), the system will then perform the calculations of the algorithms shown in Box 70.

The first algorithm, shown below:

$$Dep=((E_{HH}+E_{HL})-(E_{LH}+E_{LL}))/(2dp)$$

is used to determine the change in energy due to pressure (Dep).

The second algorithm, shown below:

$$Def=((E_{HH}+E_{LH})-(E_{HL}+E_{LL}))/(2df)$$

is used to determine the change in energy due to frequency (Def).

The third algorithm, shown below:

$$Dsp=((m_{HH}+m_{HL})-(m_{LH}+m_{LL}))/(2dp)$$

is used to determine the change in slope due to pressure (Dsp).

The fourth algorithm, shown below:

$$Dsf=((m_{HH}+m_{LH})-(m_{HL}+m_{LL}))/(2df)$$

is used to determine the change in slope due to frequency (Dsf).

The fifth algorithm, shown below:

$$E1=\text{average }(E_{HH}, E_{HL}, E_{LH}, E_{LL})$$

is used to determine the average energy for the high pressure/high frequency, high pressure/low frequency, low pressure/high frequency, and low pressure/low frequency conditions.

The sixth algorithm, shown below:

$$S1=\text{average }(m_{HH}, m_{HL}, m_{LH}, m_{LL})$$

is used to determine the average slope for the high pressure/high frequency, high pressure/low frequency, low pressure/high frequency, and low pressure/low frequency conditions.

The seventh algorithm, shown below:

$$E2=E1+(E_{DESIRED}-E1)/n$$

wherein n is greater than 1, is used to determine the new target energy (E2). It should be noted that the desired energy ($E_{DESIRED}$) is pre-selected by the operator.

The eighth algorithm, shown below:

$$S2=S1+(S_{DESIRED}-S1)/n$$

wherein n is greater than 1, is used to determine the new target slope (S2). It should be noted that the desired slope ($S_{DESIRED}$) is pre-selected by the operator.

The ninth algorithm, shown below:

$$F_{NEW}=[(DspE2-DspE1-DepS2+DepS1-DepDsfF)/(DefDsp-DepDsf)]$$

is used to determine the new target frequency ($F_{NEW}$) to achieve the new target energy (E2). Once the $F_{NEW}$ is determined, it replaces F as the default frequency.

The tenth algorithm, shown below:

$$P_{NEW}=[(DsfE2-DsfE1-DefS2+DefS1+DepDsfP-DefDspP)/(DefDsp-DepDsf)]$$

is used to determine the new target pressure ($P_{NEW}$) to achieve the new target slope (S2). Once the $P_{NEW}$ is determined, it replaces P as the default pressure.

Once all of the calculations have been performed for the above-described algorithms, the system is then prompted to determine whether the $E_{DESIRED}$ and the $S_{DESIRED}$ conditions have been satisfied, as shown in Box 80. The determination with respect to the $E_{DESIRED}$ and the $S_{DESIRED}$ conditions are calculated according to the following formulas:

$$E_{LL}<E_{DESIRED}<E_{HH}$$

and $$m_{LL}<S_{DESIRED}<m_{HH}$$

wherein if both the $E_{DESIRED}$ and the $S_{DESIRED}$ conditions fall between their respective formulaic extremes, the system is prompted to narrow the search, as shown in Box 90. The search is narrowed by dividing the dp and the df by n, respectively, wherein n is a number greater than 1. This has the intended effect of decreasing the amount of change in pressure and frequency, thus reducing the $E_{LL}/E_{HH}$ and $m_{LL}/m_{HH}$ ranges, respectively. The entire cycle is then repeated (starting at Box 20) with the new pressure and frequency defaults (i.e., $P_{NEW}$ and $F_{NEW}$), and is continued until the $E_{DESIRED}$ and the $S_{DESIRED}$ fall within the narrowed $E_{LL}/E_{HH}$ and $m_{LL}/m_{HH}$ ranges, respectively. By way of a non-limiting example, the cycle could be repeated until the narrowed $E_{LL}/E_{HH}$ and $m_{LL}/m_{HH}$ ranges are within a pre-selected percentage of the $E_{DESIRED}$ and the $S_{DESIRED}$, respectively. This process is continuously repeated during the operation of the apparatus to ensure that both the $E_{DESIRED}$ and the $S_{DESIRED}$ fall within the narrowed $E_{LL}/E_{HH}$ and $m_{LL}/m_{HH}$ ranges.

However, if either one of the $E_{DESIRED}$ and the $S_{DESIRED}$ conditions do not fall between their respective formulaic extremes, the system is prompted to expand the search, as shown in Box 100. The search is expanded by either multiplying the dp and the df by n (wherein n is a number greater than 1), respectively, depending on whether the $E_{DESIRED}$ or the $S_{DESIRED}$ fell outside of the respective range. This has the intended effect of increasing the amount of change in pressure and/or frequency thus increasing the $E_{LL}/E_{HH}$ and/or $m_{LL}/m_{HH}$ ranges, respectively. The entire cycle is then repeated (starting at Box 20) with the new pressure and frequency defaults (i.e., $P_{NEW}$ and $F_{NEW}$) and is continued until the $E_{DESIRED}$ and/or the $S_{DESIRED}$ fall within the narrowed $E_{LL}/E_{HH}$ and/or $m_{LL}/m_{HH}$ ranges, respectively. By way of a non-limiting example, the cycle could be repeated until the expanded $E_{LL}/E_{HH}$ and $m_{LL}/m_{HH}$ ranges are within a pre-selected percentage of the $E_{DESIRED}$ and the $S_{DESIRED}$, respectively. This process is continuously repeated during the operation of the apparatus to ensure that both the $E_{DESIRED}$ and the $S_{DESIRED}$ fall within the narrowed $E_{LL}/E_{HH}$ and $m_{LL}/m_{HH}$ ranges.

In accordance with another embodiment of the present invention, a pressure dither system is provided for use in conjunction with a failure mode testing system. The pressure dither system will overcome the previously described problem of actuators having a tendency, due to frictional forces and historesis, to gravitate towards a set point and get stuck, thus causing the actuators to improperly function.

Pressure dither involves the application and/or subtraction of a small amount of pressure to or from the cylinder, generally on the order of about 1–2 psi, either above or below the default pressure P and the change in pressure dp.

The reason for employing a pressure dither is enhanced controllability. If the cylinder of the actuator is constantly at a fixed pressure, even when running at the "high" pressure condition, it will gravitate to a set point and get stuck, as previously described. By dithering the pressure a slight amount, i.e., fluctuating the pressure slightly, this unwanted situation can be avoided. Specifically, the extension and/or retraction pressure of the actuator cylinder is preferably slightly different (i.e., higher and/or lower as compared to the fixed pressure) during each cycle, therefore, the probability that the cylinder will get stuck is decreased. It should be noted that the pressure dither system can be used either independent of, or in conjunction with the control system of the present invention.

Figure 2:
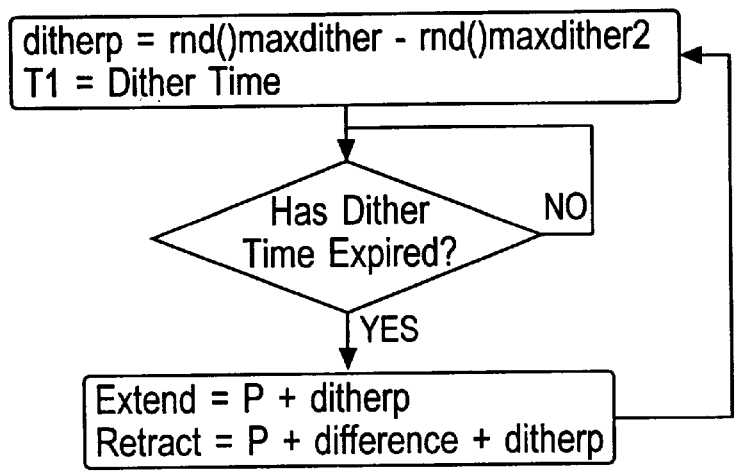
FIG. 2 is a schematic of a pressure dither system for a failure mode testing system, in accordance with one aspect of the present invention.

With reference to FIG. 2, there is illustrated a schematic view of pressure dither system for a failure mode testing system, in accordance with one embodiment of the present invention. The pressure dither system can be incorporated into a software program that can be employed to control and operate the failure mode testing system.

By way of a non-limiting example, an algorithm for determining pressure dither (ditherp) is shown below:

ditherp=[((rnd)(maxdither))−((rnd)(maxdither2))]

wherein rnd is a random number function between 0 and 1, and maxdither is the pre-selected maximum pressure difference for pressure dither (ditherp).

By way of a non-limiting example, the ditherp could be expressed as follows, assuming a rnd=1 and a maxdither of 1 psi were employed:

ditherp=[(1)(1 psi)]−[(1)(1 psi)(2)]=−0.5 psi

Thus, the ditherp would be −0.5 psi in this case, meaning that the pressure to the cylinder would be dithered by −0.5 psi. once the ditherp has been determined, the pressure during the extend phase (Extend) and retract phase (Retract) can then be calculated according to the following algorithms:

Extend=P+ditherp wherein P is the default pressure, and ditherp is the pressure dither, and Retract=P+difference+ditherp wherein P is the default pressure, difference is a pre-selected pressure difference between the extend and retract pressures, and ditherp is the pressure dither.

By way of a non-limiting example, the Extend pressure could be expressed as follows, assuming a P=30 psi and a ditherp of −0.5 psi were employed:

Extend=30 psi+(−0.5 psi)=29.5 psi

By way of a non-limiting example, the Retract pressure could be expressed as follows, assuming a P=30 psi, a difference (i.e., pressure difference between the extend and retract pressures) of 5 psi, and a ditherp of −0.5 psi were employed:

Retract=30 psi+5 psi+(−0.5 psi)=34.5 psi

Although the afore-mentioned pressure dither system algorithms are especially suited for creating and maintaining the pressure dither system of the present invention, it should be noted that any other suitable system or method for altering or changing the default pressure supplied to the cylinder can be employed as well.

In accordance with yet another embodiment of the present invention, a frequency ringing system is provided for use in conjunction with a failure mode testing system. The frequency ringing system will overcome the previously described problem of actuators receiving less energy than the other actuators, causing the apparatus to drift toward the actuator having the lowest energy level, resulting in performance problems.

The frequency ringing system involves reordering the frequency assigned to a particular cylinder. The reordering can either be random or cycled. The frequency ringing system does not involve changing the amount of any particular frequency itself (that is controlled by the control system, specifically the control algorithm), but only the location of where that frequency is vis-a-vis the cylinders.

To illustrate this concept, consider the following non-limiting example. Assume that the six actuator cylinders are assigned the following respective frequencies: Cylinder 1—2 Hz; Cylinder 2—2.5 Hz, Cylinder 3—3 Hz; Cylinder 4—3.5 Hz, Cylinder 5—4 Hz; and Cylinder 6—4.5 Hz. Now, if these frequencies did not change during the course of the testing procedure, the apparatus would have a tendency to drift towards Cylinder 1, as it has the lowest frequency, and as explained previously, the lowest energy. Therefore, the present invention overcomes this problem by indexing, reordering or reassigning the various frequencies, regardless of their magnitude, to each of the cylinders so that no one cylinder remains at the same frequency for any extended period of time. It should be noted that present invention does not employ a simple rotation of the frequencies, i.e., moving the frequencies in order around the adjacent actuators, as that permits the formation of a "moving" or "roving" low energy actuator location. Therefore, instead of the low energy actuator being found at one particular actuator location, the low energy actuator is moving around all six actuator locations in sequence. The reordering of the frequencies, in accordance with present invention, avoids this problem.

The time interval between the random assignments can be for any length and can be either fixed or random. To illustrate this concept, assume that the cylinders originally are set at the following frequencies: Cylinder 1—2 Hz;

Cylinder 2—2.5 Hz, Cylinder 3—3 Hz; Cylinder 4—3.5 Hz, Cylinder 5—4 Hz; and Cylinder 6—4.5 Hz, and that the frequency ringing system has been programmed to randomly reorder the frequencies every one second, for a total of six seconds. As a non-limiting example, the frequency information for each cylinder could look like that presented in Table 1 below:

TABLE 1

| Cyl. # | Init. Freq. (Hz) | Time1 Freq. (Hz) | Time2 Freq. (Hz) | Time3 Freq. (Hz) | Time4 Freq. (Hz) | Time5 Freq. (Hz) | Time6 Freq. (Hz) |
|---|---|---|---|---|---|---|---|
| 1 | 2 | 2.5 | 4.5 | 3 | 4 | 3.5 | 2 |
| 2 | 2.5 | 4.5 | 2 | 4 | 3 | 2.5 | 3.5 |
| 3 | 3 | 2 | 3.5 | 2.5 | 4.5 | 3 | 4 |
| 4 | 3.5 | 3 | 2.5 | 3.5 | 2 | 4 | 4.5 |
| 5 | 4 | 3.5 | 4 | 2 | 2.5 | 4.5 | 3 |
| 6 | 4.5 | 4 | 3 | 4.5 | 3.5 | 2 | 2.5 |

As can be seen from Table 1, the cylinder location of the frequencies listed above differ after each second has elapsed, therefore, no one cylinder retains the same frequency for any extended period of time. It should be noted that the frequency ringing system can be used either independent of, or in conjunction with either the control system and/or the pressure dither system of the present invention.

Figure 3:
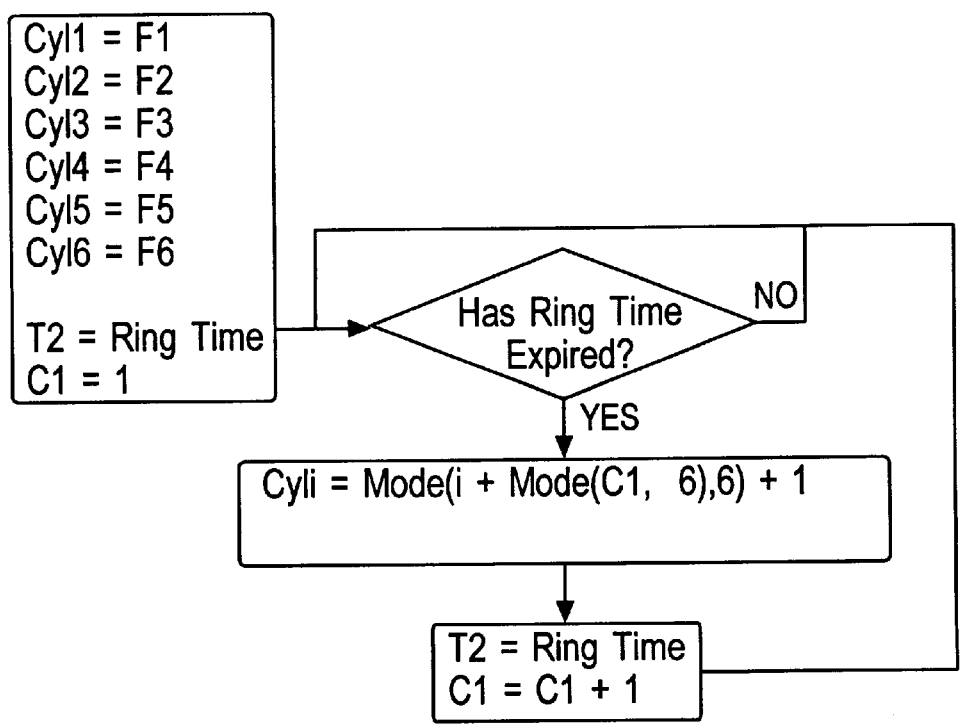
FIG. 3 is a schematic of a frequency ringing system for a failure mode testing system, in accordance with one aspect of the present invention.

With reference to FIG. 3, there is illustrated a schematic view of frequency ringing system for a failure mode testing system, in accordance with one embodiment of the present invention. The frequency ringing system can be incorporated into a software program that can be employed to control and operate the failure mode testing system.

By way of a non-limiting example, an algorithm for determining frequency ringing is shown below:

$$\text{Cylinder } i = \text{Mode}(i + \text{Mode}(C1, 6), 6) + 1$$

wherein i is the cylinder number (i.e., a number between 1 and 6), Mode is the remainder of the quotient between any two given numbers, and C1 is the count number (e.g., any number representing a status change in the cylinder frequency location). Thus, count 1 is denoted herein as C1, count 2 is denoted as C2, and so forth. Each cylinder is assigned an initial frequency (e.g., cylinder 1 is assigned frequency 1 (F1), cylinder 2 is assigned frequency 2 (F2), and so forth); thus, as the frequency is indexed or reordered at each count, the frequency assigned to a particular cylinder is changed (which can be abbreviated as cyli).

By way of a non-limiting example, the frequency ringing system as applied to cylinders 1–6 through an eight count series (e.g., 1–8) is illustrated below:

Count 1
  Cylinder 1=Mode(1+Mode(1,6),6)+1
  Cylinder 1=Mode(1+1,6)+1
  Cylinder 1=Mode(2,6)+1
  Cylinder 1=2+1
  Cylinder 1=3.
  Thus, cylinder 1 at count 1 is assigned frequency 3.
Count 2
  Cylinder 1=Mode(1+Mode(2, 6),6)+1
  Cylinder 1=Mode(1+2,6)+1
  Cylinder 1=Mode(3,6)+1
  Cylinder 1=3+1
  Cylinder 1=4.
  Thus, cylinder 1 at count 2 is assigned frequency 4.
Count 3
  Cylinder 1=Mode(1+Mode(3, 6),6)+1
  Cylinder 1=Mode(1+3,6)+1
  Cylinder 1=Mode(4,6)+1
  Cylinder 1=4+1
  Cylinder 1=5.
  Thus, cylinder 1 at count 3 is assigned frequency 5.
Count 4
  Cylinder 1=Mode(1+Mode(4, 6),6)+1
  Cylinder 1=Mode(1+4,6)+1
  Cylinder 1=Mode(5,6)+1
  Cylinder 1=5+1
  Cylinder 1=6.
  Thus, cylinder 1 at count 4 is assigned frequency 6.
Count 5
  Cylinder 1=Mode(1+Mode(5, 6),6)+1
  Cylinder 1=Mode(1+5,6)+1
  Cylinder 1=Mode(6,6)+1
  Cylinder 1=0+1
  Cylinder 1=1.
  Thus, cylinder 1 at count 5 is assigned frequency 1.
Count 6
  Cylinder 1=Mode(1+Mode(6, 6),6)+1
  Cylinder 1=Mode(1+0,6)+1
  Cylinder 1=Mode(1,6)+1
  Cylinder 1=1+1
  Cylinder 1=2.
  Thus, cylinder 1 at count 6 is assigned frequency 2.
Count 7
  Cylinder 1=Mode(1+Mode(7, 6),6)+1
  Cylinder 1=Mode(1+7,6)+1
  Cylinder 1=Mode(8,6)+1
  Cylinder 1=2+1
  Cylinder 1=3.
  Thus, cylinder 1 at count 7 is assigned frequency 3.
Count 8
  Cylinder 1=Mode(1+Mode(8, 6),6)+1
  Cylinder 1=Mode(1+8,6)+1
  Cylinder 1=Mode(9,6)+1
  Cylinder 1=3+1
  Cylinder 1=4.
  Thus, cylinder 1 at count 8 is assigned frequency 4.

By way of a non-limiting example, the frequency ringing system as applied to cylinder 2 through an eight count series (e.g., 1–8) is illustrated below:
Count 1
  Cylinder 2=Mode(2+Mode(1, 6),6)+1
  Cylinder 2=Mode(2+1,6)+1
  Cylinder 2=Mode(3,6)+1
  Cylinder 2=3+1
  Cylinder 2=4.
  Thus, cylinder 2 at count 1 is assigned frequency 4.
Count 2
  Cylinder 2=Mode(2+Mode(2, 6),6)+1
  Cylinder 2=Mode(2+2,6)+1
  Cylinder 2=Mode(4,6)+1
  Cylinder 2=4+1
  Cylinder 2=5.
  Thus, cylinder 2 at count 2 is assigned frequency 5.

Count 3
    Cylinder 2=Mode(2+Mode(3, 6),6) 1
    Cylinder 2=Mode(2+3,6)+1
    Cylinder 2=Mode(5,6)+1
    Cylinder 2=5+1
    Cylinder 2=6.
    Thus, cylinder 2 at count 3 is assigned frequency 6.
Count 4
    Cylinder 2=Mode(2+Mode(4, 6),6)+1
    Cylinder 2=Mode(2+4,6)+1
    Cylinder 2=Mode(6,6)+1
    Cylinder 2=0+1
    Cylinder 2=1.
    Thus, cylinder 2 at count 4 is assigned frequency 1.
Count 5
    Cylinder 2=Mode(2+Mode(5, 6),6)+1
    Cylinder 2=Mode(2+5,6)+1
    Cylinder 2=Mode(7,6)+1
    Cylinder 2=1+1
    Cylinder 2=2.
    Thus, cylinder 2 at count 5 is assigned frequency 2.
Count 6
    Cylinder 2=Mode(2+Mode(6, 6),6)+1
    Cylinder 2=Mode(2+0,6)+1
    Cylinder 2=Mode(2,6)+1
    Cylinder 2=2+1
    Cylinder 2=3.
    Thus, cylinder 2 at count 6 is assigned frequency 3.
Count 7
    Cylinder 2=Mode(2+Mode(7, 6),6)+1
    Cylinder 2=Mode(2+7,6)+1
    Cylinder 2=Mode(9,6)+1
    Cylinder 2=3+1
    Cylinder 2=4.
    Thus, cylinder 2 at count 7 is assigned frequency 4.
Count 8
    Cylinder 2=Mode(2+Mode(8, 6),6)+1
    Cylinder 2=Mode(2+8,6)+1
    Cylinder 2=Mode(10,6)+1
    Cylinder 2=4+1
    Cylinder 2=5.
    Thus, cylinder 2 at count 8 is assigned frequency 5.
By way of a non-limiting example, the frequency ringing system as applied to cylinder 3 through an eight count series (e.g., 1–8) is illustrated below:
Count 1
    Cylinder 3=Mode(3+Mode(1, 6),6)+1
    Cylinder 3=Mode(3+1,6)+1
    Cylinder 3=Mode(4,6)+1
    Cylinder 3=4+1
    Cylinder 3=5.
    Thus, cylinder 3 at count 1 is assigned frequency 5.
Count 2
    Cylinder 3=Mode(3+Mode(2, 6),6)+1
    Cylinder 3=Mode(3+2,6)+1
    Cylinder 3=Mode(5,6)+1
    Cylinder 3=5+1
    Cylinder 3=6.
    Thus, cylinder 3 at count 2 is assigned frequency 6.

Count 3
    Cylinder 3=Mode(3+Mode(3, 6),6)+1
    Cylinder 3=Mode(3+3,6)+1
    Cylinder 3=Mode(6,6)+1
    Cylinder 3=0+1
    Cylinder 3=1.
    Thus, cylinder 3 at count 3 is assigned frequency 1.
Count 4
    Cylinder 3=Mode(3 Mode(4, 6),6) 1
    Cylinder 3=Mode(3+4,6)+1
    Cylinder 3=Mode(7,6)+1
    Cylinder 3=1+1
    Cylinder 3=2.
    Thus, cylinder 3 at count 4 is assigned frequency 2.
Count 5
    Cylinder 3=Mode(3+Mode(5, 6),6)+1
    Cylinder 3=Mode(3+5,6)+1
    Cylinder 3=Mode(8,6)+1
    Cylinder 3=2+1
    Cylinder 3=3.
    Thus, cylinder 2 at count 5 is assigned frequency 3.
Count 6
    Cylinder 3=Mode(3+Mode(6, 6),6)+1
    Cylinder 3=Mode(3+0,6)+1
    Cylinder 3=Mode(3,6)+1
    Cylinder 3=3+1
    Cylinder 3=4.
    Thus, cylinder 2 at count 6 is assigned frequency 4.
Count 7
    Cylinder 3=Mode(3+Mode(7, 6),6)+1
    Cylinder 3=Mode(3+7,6)+1
    Cylinder 3=Mode(10,6)+1
    Cylinder 3=4+1
    Cylinder 3=5.
    Thus, cylinder 3 at count 7 is assigned frequency 5.
Count 8
    Cylinder 3=Mode(3+Mode(8, 6),6)+1
    Cylinder 3=Mode(3+8,6)+1
    Cylinder 3=Mode(11,6)+1
    Cylinder 3=5+1
    Cylinder 3=6.
    Thus, cylinder 3 at count 8 is assigned frequency 6.
By way of a non-limiting example, the frequency ringing system as applied to cylinder 4 through an eight count series (e.g., 1–8) is illustrated below:
Count 1
    Cylinder 4=Mode(4+Mode(1, 6),6)+1
    Cylinder 4=Mode(4+1, 6)+1
    Cylinder 4=Mode(5,6)+1
    Cylinder 4=5+1
    Cylinder 4=6.
    Thus, cylinder 4 at count 1 is assigned frequency 6.
Count 2
    Cylinder 4=Mode(4+Mode(2, 6),6)+1
    Cylinder 4=Mode(4+2,6)+1
    Cylinder 4=Mode(6,6)+1
    Cylinder 4=0+1
    Cylinder 4=1.
    Thus, cylinder 4 at count 2 is assigned frequency 1.

Count 3
　Cylinder 4=Mode(4+Mode(3, 6),6)+1
　Cylinder 4=Mode(4+3,6)+1
　Cylinder 4=Mode(7,6)+1
　Cylinder 4=1+1
　Cylinder 4=2.
　Thus, cylinder 4 at count 3 is assigned frequency 2.
Count 4
　Cylinder 4=Mode(4+Mode(4, 6),6)+1
　Cylinder 4=Mode(4+4,6)+1
　Cylinder 4=Mode(8,6)+1
　Cylinder 4=2+1
　Cylinder 4=3.
　Thus, cylinder 4 at count 4 his assigned frequency 3.
Count 5
　Cylinder 4=Mode(4+Mode(5, 6),6)+1
　Cylinder 4=Mode(4+5,6)+1
　Cylinder 4=Mode(9,6)+1
　Cylinder 4=3+1
　Cylinder 4=4.
　Thus, cylinder 4 at count 5 is assigned frequency 4.
Count 6
　Cylinder 4=Mode(4+Mode(6, 6),6)+1
　Cylinder 4=Mode(4+0,6)+1
　Cylinder 4=Mode(4,6)+1
　Cylinder 4=4+1
　Cylinder 4=5.
　Thus, cylinder 4 at count 6 is assigned frequency 5.
Count 7
　Cylinder 4=Mode(4+Mode(7, 6),6)+1
　Cylinder 4=Mode(4+1,6)+1
　Cylinder 4=Mode(5,6)+1
　Cylinder 4=5+1
　Cylinder 4=6.
　Thus, cylinder 4 at count 7 is assigned frequency 6.
Count 8
　Cylinder 4=Mode(4+Mode(8, 6),6)+1
　Cylinder 4=Mode(4+2,6)+1
　Cylinder 4=Mode(6,6)+1
　Cylinder 4=0+1
　Cylinder 4=1.
　Thus, cylinder 4 at count 8 is assigned frequency 1.

By way of a non-limiting example, the frequency ringing system as applied to cylinder 5 through a six count series (e.g., 1–6) is illustrated below:
Count 1
　Cylinder 5=Mode(5+Mode(1, 6),6)+1
　Cylinder 5=Mode(5+1,6)+1
　Cylinder 5=Mode(6,6)+1
　Cylinder 5=0+1
　Cylinder 5=1.
　Thus, cylinder 5 at count 1 is assigned frequency 1.
Count 2
　Cylinder 5=Mode(5+Mode(2, 6),6)+1
　Cylinder 5=Mode(5+2,6)+1
　Cylinder 5=Mode(7,6)+1
　Cylinder 5=1+1
　Cylinder 5=2
　Thus, cylinder 5 at count 2 is assigned frequency 2.
Count 3
　Cylinder 5=Mode(5+Mode(3, 6),6)+1
　Cylinder 5=Mode(5+3,6)+1
　Cylinder 5=Mode(8,6)+1
　Cylinder 5=2+1
　Cylinder 5=3.
　Thus, cylinder 5 at count 3 is assigned frequency 3.
Count 4
　Cylinder 5=Mode(5+Mode(4, 6),6)+1
　Cylinder 5=Mode(5+4,6)+1
　Cylinder 5=Mode(9,6)+1
　Cylinder 5=3+1
　Cylinder 5=4.
　Thus, cylinder 5 at count 4 is assigned frequency 4.
Count 5
　Cylinder 5=Mode(5+Mode(5, 6),6)+1
　Cylinder 5=Mode(5+5,6)+1
　Cylinder 5=Mode(10,6)+1
　Cylinder 5=4+1
　Cylinder 5=5.
　Thus, cylinder 5 at count 5 is assigned frequency 5.
Count 6
　Cylinder 5=Mode(5+Mode(6, 6),6)+1
　Cylinder 5=Mode(5+0,6)+1
　Cylinder 5=Mode(5,6)+1
　Cylinder 5=5+1
　Cylinder 5=6.
　Thus, cylinder 5 at count 6 is assigned frequency 6.
Count 7
　Cylinder 5=Mode(5+Mode(7, 6),6)+1
　Cylinder 5=Mode(5+1,6)+1
　Cylinder 5=Mode(6,6)+1
　Cylinder 5=0+1
　Cylinder 5=1.
　Thus, cylinder 5 at count 7 is assigned frequency 1.
Count 8
　Cylinder 5=Mode(5+Mode(8, 6),6)+1
　Cylinder 5=Mode(5+2,6)+1
　Cylinder 5=Mode(7,6)+1
　Cylinder 5=1+1
　Cylinder 5=2.
　Thus, cylinder 5 at count 8 is assigned frequency 2.

By way of a non-limiting example, the frequency ringing system as applied to cylinder 6 through an eight count series (e.g., 1–8) is illustrated below:
Count 1
　Cylinder 6=Mode(6+Mode(1, 6),6)+1
　Cylinder 6=Mode(6+1,6)+1
　Cylinder 6=Mode(7,6)+1
　Cylinder 6=1+1
　Cylinder 6=2.
　Thus, cylinder 6 at count 1 is assigned frequency 2.
Count 2
　Cylinder 6=Mode(6+Mode(2, 6),6)+1
　Cylinder 6=Mode(6+2,6)+1
　Cylinder 6=Mode(8,6)+1
　Cylinder 6=2+1
　Cylinder 6=3.
　Thus, cylinder 6 at count 2 is assigned frequency 3.

Count 3
  Cylinder 6=Mode(6+Mode(3, 6),6)+1
  Cylinder 6=Mode(6+3,6)+1
  Cylinder 6=Mode(9,6)+1
  Cylinder 6=3+1
  Cylinder 6=4.
  Thus, cylinder 6 at count 3 is assigned frequency 4.
Count 4
  Cylinder 6=Mode(6+Mode(4, 6),6)+1
  Cylinder 6=Mode(6+4,6)+1
  Cylinder 6=Mode(10,6)+1
  Cylinder 6=4+1
  Cylinder 6=5.
  Thus, cylinder 6 at count 4 is assigned frequency 5.
Count 5
  Cylinder 6=Mode(6+Mode(5, 6),6)+1
  Cylinder 6=Mode(6+5,6)+1
  Cylinder 6=Mode(11,6)+1
  Cylinder 6=5+1
  Cylinder 6=6.
  Thus, cylinder 6 at count 5 is assigned frequency 6.
Count 6
  Cylinder 6 Mode(6+Mode(6, 6),6)+1
  Cylinder 6=Mode(6+0,6)+1
  Cylinder 6=Mode(6,6)+1
  Cylinder 6=0+1
  Cylinder 6=1.
  Thus, cylinder 6 at count 6 is assigned frequency 1.
Count 7
  Cylinder 6=Mode(6+Mode(7, 6),6)+1
  Cylinder 6=Mode(6+1,6)+1
  Cylinder 6=Mode(7,6)+1
  Cylinder 6=1+1
  Cylinder 6=2.
  Thus, cylinder 6 at count 7 is assigned frequency 2
Count 8
  Cylinder 6=Mode(6+Mode(8, 6),6)+1
  Cylinder 6=Mode(6+2,6)+1
  Cylinder 6=Mode(8,6)+1
  Cylinder 6=2+1
  Cylinder 6=3.
  Thus, cylinder 6 at count 8 is assigned frequency 3.
The corresponding cylinder frequencies of the various cylinders at each of the eight counts is presented in Table 2, below:

As can be seen from Table 2, the frequency initially assigned to a particular cylinder location is being indexed or reordered among the six cylinders in such a manner that after each count, an individual cylinder's frequency has changed. Additionally, it should be noted that the frequencies are not indexed in a sequential manner such that the frequencies initially assigned to adjacent cylinders move lock step around in a circle. As previously noted, that would merely cause the low-energy site to move circularly around the actuator assemblies. The present invention avoids this problem by ensuring that, sometime during a count sequence, at least one individual cylinder has a frequency of a non-adjacent cylinder.

Thus, after each count, the frequency of a particular cylinder is changed according to the following algorithm:

$$C1 = C1 + 1$$

wherein C1 is the count number (e.g., any number representing a status change in the cylinder frequency location). Thus after count 1, the frequency of a particular cylinder would be changed to that corresponding to count 2, and so forth.

Although the afore-mentioned frequency ringing system algorithms are especially suited for creating and maintaining the frequency ringing system of the present invention, it should be noted that any other suitable system or method for indexing the frequencies assigned to the cylinders can be employed as well.

As previously mentioned, the control system, the pressure dither system, and the frequency ringing system, can be incorporated into computer software programs, either independently or combined in various combinations.

Figure 4:
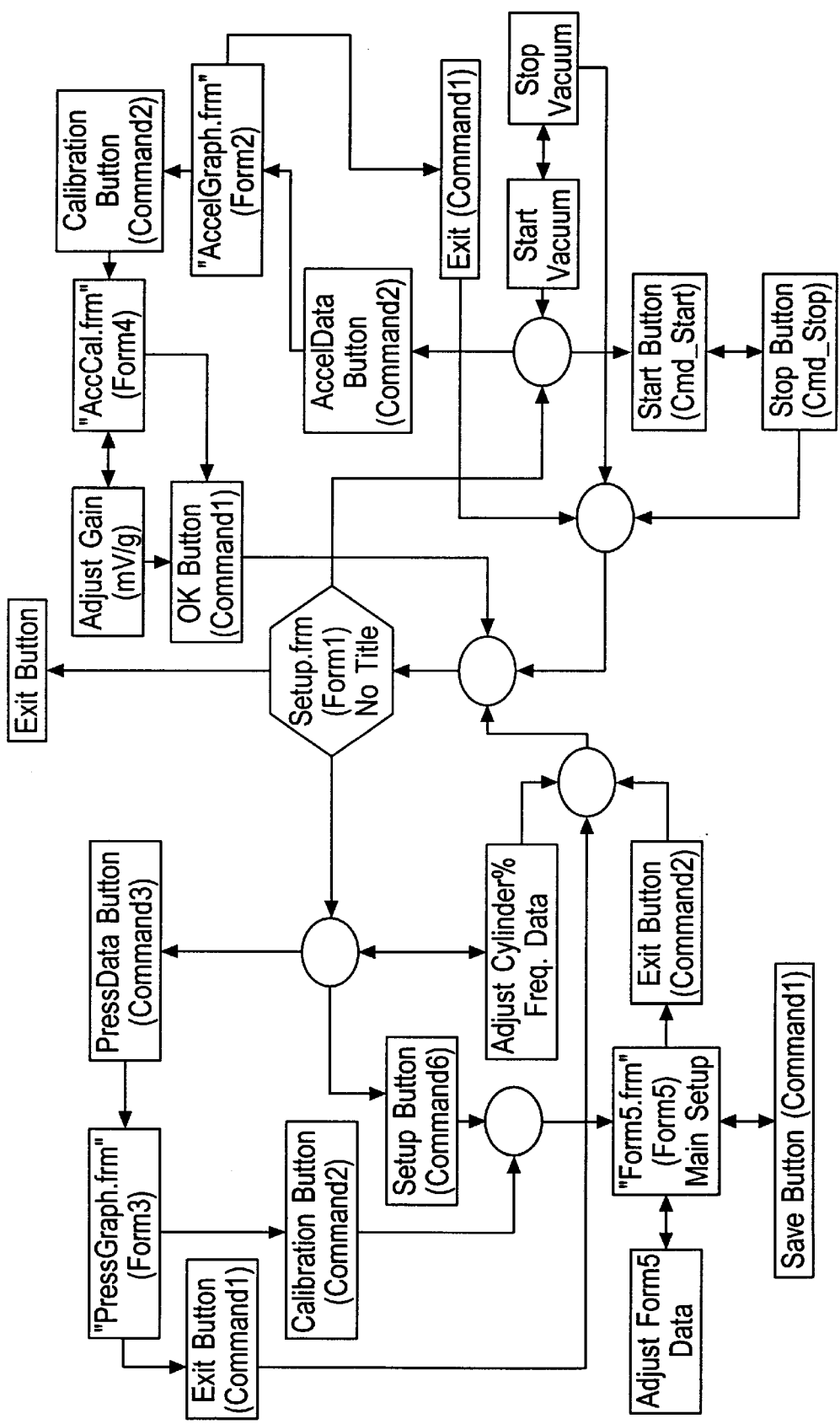
FIG. 4 is a schematic of a computer software program for a control system for a failure mode testing system, in accordance with one aspect of the present invention.

With reference to FIG. 4, there is illustrated a schematic view of a computer software program for a control system for a failure mode testing system, in accordance with one embodiment of the invention.

Figure 5:
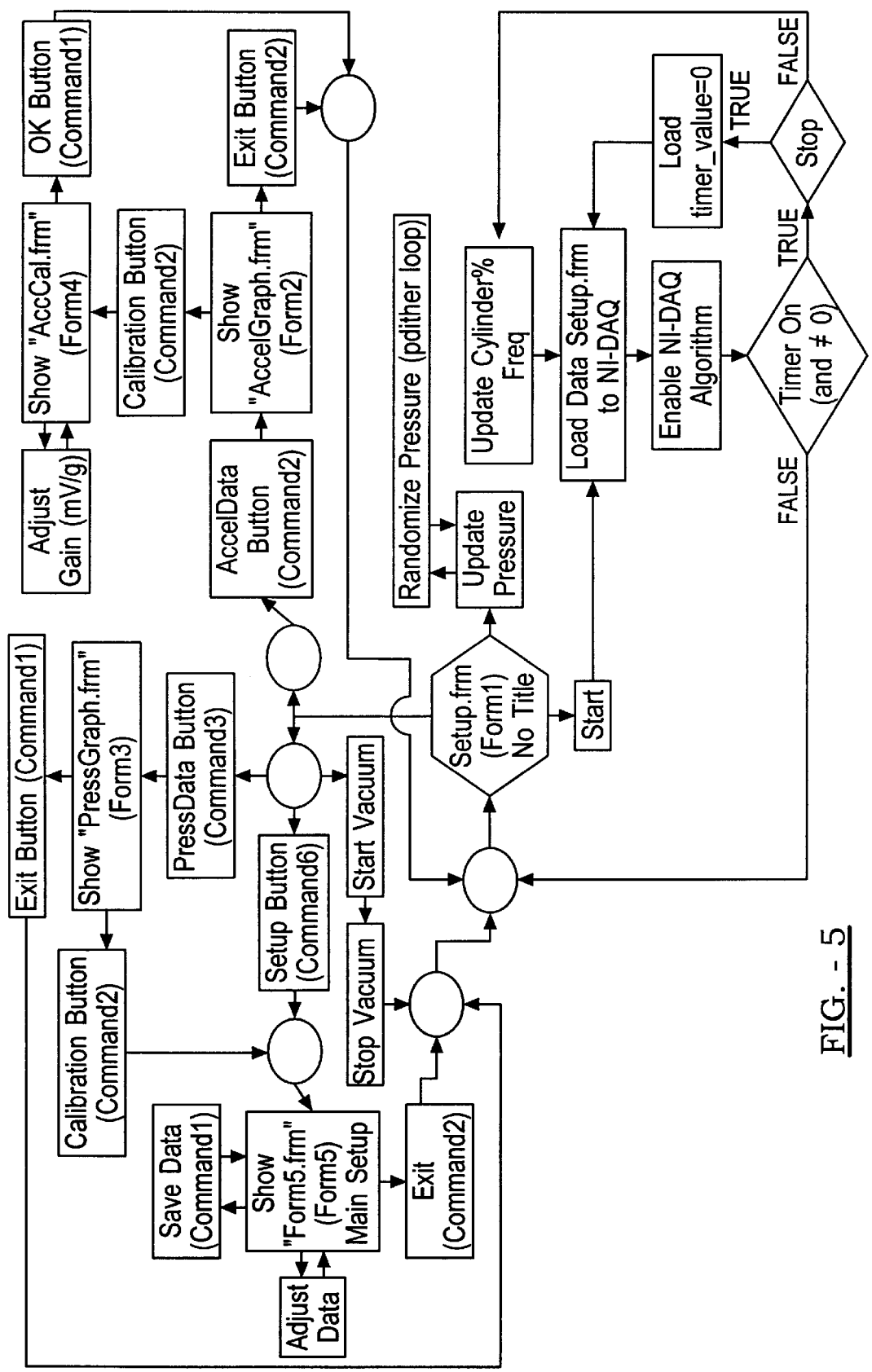
FIG. 5 is a schematic of an alternative computer software program for a control system for a failure mode testing system, in accordance with one aspect of the present invention.

With reference to FIG. 5, there is illustrated a schematic view of a computer software program for a control system for a failure mode testing system employing both a pressure dither system and a frequency ringing system, in accordance with one embodiment of the invention.

The foregoing description is considered illustrative only of the principles of the invention. Furthermore, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims which follow.

What is claimed is:

1. A control system for a failure mode testing system having a determinable system response, wherein the testing system includes a plurality of actuator cylinders, each cyl-

TABLE 2

| Cyl. # | C1 Cyl. # Freq. | C2 Cyl. # Freq. | C3 Cyl. # Freq. | C4 Cyl. # Freq. | C5 Cyl. # Freq. | C6 Cyl. # Freq. | C7 Cyl. # Freq. | C8 Cyl. # Freq. |
|---|---|---|---|---|---|---|---|---|
| 1 | 2 | 3 | 4 | 5 | 6 | 1 | 2 | 3 |
| 2 | 3 | 4 | 5 | 6 | 1 | 2 | 3 | 4 |
| 3 | 4 | 5 | 6 | 1 | 2 | 3 | 4 | 5 |
| 4 | 5 | 6 | 1 | 2 | 3 | 4 | 5 | 6 |
| 5 | 6 | 1 | 2 | 3 | 4 | 5 | 6 | 1 |
| 6 | 1 | 2 | 3 | 4 | 5 | 6 | 1 | 2 | inder operating at an initial pressure and an initial frequency, wherein the frequency of each of the cylinders is different, comprising:

a) selecting a desired energy level of the system response;

b) selecting a desired slope of the fast Fourier transform of the system response;

c) changing an operational parameter of the cylinders by a pre-selected amount in order to create a first pressure/frequency condition, wherein the operational parameter is selected from the group consisting of pressure, frequency, and combinations thereof;

d) determining the system response in terms of energy and slope of the fast Fourier transform of the system response under the first pressure/frequency condition; and e) storing the system response determination of the first pressure/frequency condition in a data storage medium.

2. The control system in accordance with claim 1, further comprising:

f) changing an operational parameter of the cylinders by a pre-selected amount in order to create a second pressure/frequency condition different from the first pressure/frequency condition;

g) determining the system response in terms of energy and slope of the fast Fourier transform of the system response under the second pressure/frequency condition; and h) storing the system response determination of the second pressure/frequency condition in a data storage medium.

3. The control system in accordance with claim 2, further comprising:

i) changing an operational parameter of the cylinders by a pre-selected amount in order to create a third pressure/frequency condition different from the first and second pressure/frequency conditions;

j) determining the system response in terms of energy and slope of the fast Fourier transform of the system response under the third pressure/frequency condition; and k) storing the system response determination of the third pressure/frequency condition in a data storage medium.

4. The control system in accordance with claim 3, further comprising:

l) changing an operational parameter of the cylinders by a pre-selected amount in order to create a fourth pressure/frequency condition different from the first, second, and third pressure/frequency conditions;

m) determining the system response in terms of energy and slope of the fast Fourier transform of the system response under the fourth pressure/frequency condition; and n) storing the system response determination of the fourth pressure/frequency condition in a data storage medium.

5. The control system in accordance with claim 4, further comprising:

o) determining whether the desired energy level of the system response falls within the range defined by the measured energy level of any of the pressure/frequency conditions according to the formula: $E_{LL}<E_{DESIRED}<E_{HH}$, wherein $E_{LL}$ is the energy measured during a pressure/frequency condition corresponding to a low pressure/low frequency condition, $E_{DESIRED}$ is the desired energy level of the system response, and $E_{HH}$ is the energy measured during a pressure/frequency condition corresponding to a high pressure/high frequency condition; and p) determining whether the desired slope of the fast Fourier transform of the system response falls within the range defined by the measured slope of the fast Fourier transform of the system response of any of the pressure/frequency conditions according to the formula: $m_{LL}<m_{DESIRED}<m_{HH}$, wherein $m_{LL}$ is the slope of the fast Fourier transform of the system response measured during a pressure/frequency condition corresponding to a low pressure/low frequency condition, $m_{DESIRED}$ is the desired slope of the fast Fourier transform of the system response of the cylinder, and $m_{HH}$ is the slope of the fast Fourier transform of the system response measured during a pressure/frequency condition corresponding to a high pressure/high frequency condition.

6. The control system in accordance with claim 5, further comprising:

q) decreasing the pre-selected amount that the operational parameter is changed by and repeating steps c) through p), if the desired energy level of the system response does fall within the range defined by the measured energy level of a pressure/frequency condition corresponding to a low pressure/low frequency condition and a pressure/frequency condition corresponding to a high pressure/high frequency condition.

7. The control system in accordance with claim 5, further comprising:

r) increasing the pre-selected amount that the operational parameter is increased by and repeating steps c) through p), if the desired energy level of the system response does not fall within the range defined by the measured energy level of a pressure/frequency condition corresponding to a low pressure/low frequency condition and a pressure/frequency condition corresponding to a high pressure/high frequency condition.

8. The control system in accordance with claim 5, further comprising:

s) decreasing the pre-selected amount that the operational parameter is changed by and repeating steps c) through p), if the desired slope of the fast Fourier transform of the system response does fall within the range defined by the measured slope of the fast Fourier transform of the system response of a pressure/frequency condition corresponding to a low pressure/low frequency condition and a pressure/frequency condition corresponding to a high pressure/high frequency condition.

9. The control system in accordance with claim 5, further comprising:

t) increasing the pre-selected amount that the operational parameter is changed by and repeating steps c) through p), if the desired slope of the fast Fourier transform of the system response does not fall within the range defined by the measured slope of the fast Fourier transform of the system response of a pressure/frequency condition corresponding to a low pressure/low frequency condition and a pressure/frequency condition corresponding to a high pressure/high frequency condition.

10. The control system in accordance with claim 5, further comprising:

u) calculating the change in energy due to pressure (Dep) according to the formula: $Dep=((E_{HH}+E_{HL})-(E_{LH}+E_{LL}))/(2dp)$, wherein $E_{HH}$ is the energy measured during a pressure/frequency condition corresponding to a high pressure/high frequency condition, $E_{HL}$ is the energy measured during a pressure/frequency condition corresponding to a high pressure/low frequency condition, $E_{LH}$ is the energy measured during a pressure/frequency condition corresponding to a low pressure/high frequency condition, $E_{LL}$ is the energy measured during a pressure/frequency condition corresponding to a low pressure/low frequency condition, and dp is the pre-selected amount by which the pressure is either increased or decreased.

11. The control system in accordance with claim 5, further comprising:
   v) calculating the change in energy due to frequency (Def) according to the formula: Def=$((E_{HH}+E_{LH})-(_{LHL}+E_{LL}))/(2df)$, wherein $E_{HH}$ is the energy measured during a pressure/frequency condition corresponding to a high pressure/high frequency condition, $E_{LH}$ is the energy measured during a pressure/frequency condition corresponding to a low pressure/high frequency condition, $E_{HL}$ is the energy measured during a pressure/frequency condition corresponding to a high pressure/low frequency condition, $E_{LL}$ is the energy measured during a pressure/frequency condition corresponding to a low pressure/low frequency condition, and df is the pre-selected amount by which the frequency is either increased or decreased.

12. The control system in accordance with claim 5, further comprising:
   w) calculating the change in slope of the fast Fourier transform of the frequency due to pressure (Dsp) according to the formula: Dsp=$((m_{HH}+m_{HL})-(m_{LH}+m_{LL}))/(2dp)$, wherein $m_{HH}$ is the slope of the fast Fourier transform of the system response measured during a pressure/frequency condition corresponding to a high pressure/high frequency condition, $m_{HL}$ is the slope of the fast Fourier transform of the system response measured during a pressure/frequency condition corresponding to a high pressure/low frequency condition, $m_{LH}$ is the slope of the fast Fourier transform of the system response measured during a pressure/frequency condition corresponding to a low pressure/high frequency condition, $m_{LL}$ is the slope of the fast Fourier transform of the system response measured during a pressure/frequency condition corresponding to a low pressure/low frequency condition, and dp is the pre-selected amount by which the pressure is either increased or decreased.

13. The control system in accordance with claim 5, further comprising:
   x) calculating the change in slope of the fast Fourier transform of the system response due to frequency (Dsf) according to the formula: Dsf=$((m_{HH}+m_{LH})-(m_{HL}+m_{LL}))/(2df)$, wherein $m_{HH}$ is the slope of the fast Fourier transform of the system response measured during a pressure/frequency condition corresponding to a high pressure/high frequency condition, $m_{LH}$ is the slope of the fast Fourier transform of the system response measured during a pressure/frequency condition corresponding to a low pressure/high frequency condition, $m_{HL}$ is the slope of the fast Fourier transform of the system response measured during a pressure/frequency condition corresponding to a high pressure/low frequency condition, $m_{LL}$ is the slope of the fast Fourier transform of the system response measured during a pressure/frequency condition corresponding to a low pressure/low frequency condition, and df is the pre-selected amount by which the frequency is either increased or decreased.

14. The control system in accordance with claim 5, further comprising:
   y) calculating the average energy (E1) according to the following formula: E1=average $(E_{HH}, E_{HL}, E_{LH}, E_{LL})$, wherein $E_{HH}$ is the energy measured during a pressure/frequency condition corresponding to a high pressure/high frequency condition, $E_{HL}$ is the energy measured during a pressure/frequency condition corresponding to a high pressure/low frequency condition, $E_{LH}$ is the energy measured during a pressure/frequency condition corresponding to a low pressure/high frequency condition, and $E_{LL}$ is the energy measured during a pressure/frequency condition corresponding to a low pressure/low frequency condition.

15. The control system in accordance with claim 14, further comprising:
   z) calculating the new target energy (E2) according to the following formula: E2=E1+$(E_{DESIRED}-E1)/n$, wherein E1 is the average energy, $E_{DESIRED}$ is the desired energy level of the cylinder, and n is a number greater than 1.

16. The control system in accordance with claim 15, further comprising:
   aa) calculating the average slope of the fast Fourier transform of the system response (S1) according to the following formula: S1=average $(m_{HH}, m_{HL}, m_{LH}, m_{LL})$, wherein $m_{HH}$ is the slope of the fast Fourier transform of the system response measured during a pressure/frequency condition corresponding to a high pressure/high frequency condition, $m_{HL}$ is the slope of the fast Fourier transform of the system measured during a pressure/frequency condition corresponding to a high pressure/low frequency condition, $m_{LH}$ is the slope of the fast Fourier transform of the system response measured during a pressure/frequency condition corresponding to a low pressure/high frequency condition, and $m_{LL}$ is the slope of the fast Fourier transform of the system response measured during a pressure/frequency condition corresponding to a low pressure/low frequency condition.

17. The control system in accordance with claim 16, further comprising:
   bb) calculating the new target slope of the fast Fourier transform of the system response (S2) according to the following formula: S2=S1+$(S_{DESIRED}-S1)/n$, wherein S1 is the average slope of the fast Fourier transform of the system response, $S_{DESIRED}$ is the desired slope of the fast Fourier transform of the system response, and n is a number greater than 1.

18. The control system in accordance with claim 17, further comprising:
   cc) calculating the new target pressure ($P_{NEW}$) according to the formula: $P_{NEW}$=[(DsfE2−DsfE1−DefS2+DefS1−DepDsfP)/(DefDsp−DepDsf)], wherein Def is the change in energy due to frequency, Dep is the change in energy due to pressure, Dsf is the change in slope of the fast Fourier transform of the system response due to frequency, Dsp is the change in slope of the fast Fourier transform of the system response due to pressure, E1 is the average energy, E2 is the new target energy, S1 is the average slope of the fast Fourier transform of the system response, and S2 is the new target slope of the fast Fourier transform of the system response.

19. The control system in accordance with claim 18, further comprising:

dd) substituting the new target pressure ($P_{NEW}$) for the initial pressure and repeating steps c) through p).

20. The control system in accordance with claim 17, further comprising:

ee) calculating the new target frequency ($F_{NEW}$) according to the formula: $F_{NEW}$=[(DspE2−DspE1−DepS2+DepS1−DepDsfF)/(DefDsp−DepDsf)], wherein Def is the change in energy due to frequency, Dep is the change in energy due to pressure, Dsf is the change in slope of the fast Fourier transform of the system response due to frequency, Dsp is the change in slope of the fast Fourier transform of the system response due to pressure, E1 is the average energy, E2 is the new target energy, S1 is the average slope of the fast Fourier transform of the system response, and S2 is the new target slope of the fast Fourier transform of the system response.

21. The control system in accordance with claim 20, further comprising:

ff) substituting the new target frequency ($F_{NEW}$) for the initial frequency and repeating steps c) through p).

22. The control system in accordance with claim 1, further comprising:

a pressure dither system, wherein the pressure of the actuator cylinder during extension and retraction is changed by an incremental amount of pressure (ditherp).

23. The control system in accordance with claim 22, wherein the dither pressure (ditherp) is calculated in accordance with the formula: [((rnd)(maxdither))−((rnd)(maxdither2))], wherein rnd is a random number function between 0 and 1, and maxdither is the pre-selected maximum pressure difference for dither pressure (ditherp).

24. The control system in accordance with claim 1, further comprising:

a frequency ringing system, wherein the location of a particular frequency is reordered among the plurality of actuator cylinders.

25. The control system in accordance with claim 24, wherein the frequency ringing system is calculated in accordance with the formula: cylinder i=Mode(i +Mode(C1, 6),6)+1, wherein i is the cylinder number, Mode is the remainder of the quotient between any two given numbers, and C1 is the count number representing a status change in the cylinder frequency location.

26. A control system for a failure mode testing system having a determinable system response, wherein the testing system includes a plurality of actuator cylinders, each cylinder operating at a pressure and a frequency, wherein the frequency of each of the cylinders is different, comprising:

a) selecting a desired energy level of the system response;

b) selecting a desired slope of the fast Fourier transform of the system response;

c) determining the energy level under a high pressure/high frequency condition and a low pressure/low frequency condition so as to define an energy level range;

d) determining the slope of the fast Fourier transform of the system response under a high pressure/high frequency condition and a low pressure/low frequency condition so as to define a slope range;

e) determining whether the desired energy level falls within the energy level range; and f) determining whether the desired slope of the fast Fourier transform of the system response falls within the slope range.

27. The control system in accordance with claim 26, further comprising:

g) decreasing the pressure and repeating steps a) through f), if the desired energy level of the system response does fall within the energy level range.

28. The control system in accordance with claim 26, further comprising:

h) increasing the pressure and repeating steps a) through f), if the desired energy level of the system response does not fall within the energy level range.

29. The control system in accordance with claim 26, further comprising:

i) decreasing the frequency and repeating steps a) through f), if the desired slope of the fast Fourier transform of the system response does fall within the slope range.

30. The control system in accordance with claim 26, further comprising:

j) increasing the frequency and repeating steps a) through f), if the desired slope of the fast Fourier transform of the system response does not fall within the slope range.

31. The control system in accordance with claim 26, further comprising:

a pressure dither system, wherein the pressure of the actuator cylinder during extension and retraction is changed by an incremental amount of pressure (ditherp).

32. The control system in accordance with claim 31, wherein the dither pressure (ditherp) is calculated in accordance with the formula: [((rnd)(maxdither))−((rnd)(maxdither2))], wherein rnd is a random number function between 0 and 1, and maxdither is the pre-selected maximum pressure difference for dither pressure (ditherp).

33. The control system in accordance with claim 26, further comprising:

a frequency ringing system, wherein the location of a particular frequency is reordered among the plurality of actuator cylinders.

34. The control system in accordance with claim 33, wherein the frequency ringing system is calculated in accordance with the formula: cylinder i =Mode(i+Mode(C1, 6),6)+1, wherein i is the cylinder number, Mode is the remainder of the quotient between any two given numbers, and C1 is the count number representing a status change in the cylinder frequency location.

35. A control system for a failure mode testing system having a plurality of actuator cylinders, each cylinder operating at a pressure and a frequency, wherein the frequency of each of the cylinders is different, wherein the energy level and slope of the fast Fourier transform of the frequency are capable of changing in response to pressure and frequency, comprising:

calculating the change in energy due to pressure (Dep) according to the formula: Dep=(($E_{HH}$+$E_{HL}$)−($E_{LH}$+$E_{LL}$))/(2dp), wherein $E_{HH}$ is the energy measured during a pressure/frequency condition corresponding to a high pressure/high frequency condition, $E_{HL}$ is the energy measured during a pressure/frequency condition corresponding to a high pressure/low frequency condition, $E_{LH}$ is the energy measured during a pressure/frequency condition corresponding to a low pressure/high frequency condition, $E_{LL}$ is the energy measured during a pressure/frequency condition corresponding to a low pressure/low frequency condition, and dp is the pre-selected amount by which the pressure is either increased or decreased.

36. A control system for a failure mode testing system having a determinable system response, wherein the testing system includes a plurality of actuator cylinders, each cylinder operating at a pressure and a frequency, wherein the frequency of each of the cylinders is different, wherein the energy level and slope of the fast Fourier transform of the system response are capable of changing in response to pressure and frequency, comprising:

calculating the change in energy due to frequency (Def) according to the formula: Def=$((E_{HH}+E_{LH})-(E_{HL}+E_{LL}))/(2df)$, wherein $E_{HH}$ is the energy measured during a pressure/frequency condition corresponding to a pressure/high frequency condition, $E_{LH}$ is the energy measured during a pressure/frequency condition corresponding to a low pressure/high frequency condition, $E_{HL}$ is the energy measured during a pressure/frequency condition corresponding to a high pressure/low frequency condition, $E_{LL}$ is the energy measured during a pressure/frequency condition corresponding to a low pressure/low frequency condition, and df is the pre-selected amount by which the frequency is either increased or decreased.

37. A control system for a failure mode testing system having a determinable system response, wherein the testing system includes a plurality of actuator cylinders, each cylinder operating at a pressure and a frequency, wherein the frequency of each of the cylinders is different, wherein the energy level and slope of the fast Fourier transform of the system response are capable of changing in response to pressure and frequency, comprising:

calculating the change in slope of the fast Fourier transform of the system response due to pressure (Dsp) according to the formula: Dsp=$((m_{HH}+m_{HL})-(m_{LH}+m_{LL}))/(2dp)$, wherein $m_{HH}$ is the slope of the fast Fourier transform of the system response measured during a pressure/frequency condition corresponding to a high pressure/high frequency condition, $m_{HL}$ is the slope of the fast Fourier transform of the system response measured during a pressure/frequency condition corresponding to a high pressure/low frequency condition, $m_{LH}$ is the slope of the fast Fourier transform of the system response measured during a pressure/frequency condition corresponding to a low pressure/high frequency condition, $m_{LL}$ is the slope of the fast Fourier transform of the system response measured during a pressure/frequency condition corresponding to a low pressure/low frequency condition, and dp is the pre-selected amount by which the pressure is either increased or decreased.

38. A control system for a failure mode testing system having a determinable system response, wherein the testing system includes a plurality of actuator cylinders, each cylinder operating at a pressure and a frequency, wherein the frequency of each of the cylinders is different, wherein the energy level and slope of the fast Fourier transform of the system response are capable of changing in response to pressure and frequency, comprising:

calculating the change in slope of the fast Fourier transform of the system response due to frequency (Dsf) according to the formula: Dsf=$((m_{HH}+m_{LH})-(m_{HL}+m_{LL}))/(2df)$, wherein $m_{HH}$ is the slope of the fast Fourier transform of the system response measured during a pressure/frequency condition corresponding to a high pressure/high frequency condition, $m_{LH}$ is the slope of the fast Fourier transform of the system response measured during a pressure/frequency condition corresponding to a low pressure/high frequency condition, $m_{HL}$ is the slope of the fast Fourier transform of the system response measured during a pressure/frequency condition corresponding to a high pressure/low frequency condition, $m_{LL}$ is the slope of the fast Fourier transform of the system response measured during a pressure/frequency condition corresponding to a low pressure/low frequency condition, and df is the pre-selected amount by which the frequency is either increased or decreased.

39. A control system for a failure mode testing system having a determinable system response, wherein the testing system includes a plurality of actuator cylinders, each cylinder operating at a pressure and a frequency, wherein the frequency of each of the cylinders is different, wherein the energy level and slope of the fast Fourier transform of the system response are capable of changing in response to pressure and frequency, comprising:

calculating the average energy (E1) according to the following formula: E1=average ($E_{HH}$, $E_{HL}$, $E_{LH}$, $E_{LL}$), wherein $E_{HH}$ is the energy measured during a pressure/frequency condition corresponding to a high pressure/high frequency condition, $E_{HL}$ is the energy measured during a pressure/frequency condition corresponding to a high pressure/low frequency condition, $E_{LH}$ is the energy measured during a pressure/frequency condition corresponding to a low pressure/high frequency condition, and $E_{LL}$ is the energy measured during a pressure/frequency condition corresponding to a low pressure/low frequency condition.

40. A control system for a failure mode testing system having a determinable system response, wherein the testing system includes a plurality of actuator cylinders, each cylinder operating at a pressure and a frequency, wherein the frequency of each of the cylinders is different, wherein the energy level and slope of the fast Fourier transform of the system response are capable of changing in response to pressure and frequency, comprising:

calculating the new target energy (E2) according to the following formula: E2=E1+$(E_{DESIRED}-E1)/n$, wherein E1 is the average energy, $E_{DESIRED}$ is the desired energy level of the system response, and n is a number greater than 1.

41. A control system for a failure mode testing system having a determinable system response, wherein the testing system includes a plurality of actuator cylinders, each cylinder operating at a pressure and a frequency, wherein the frequency of each of the cylinders is different, wherein the energy level and slope of the fast Fourier transform of the system response are capable of changing in response to pressure and frequency, comprising:

calculating the average slope of the fast Fourier transform of the system response (S1) according to the following formula: S1=average ($m_{HH}$, $m_{HL}$, $m_{LH}$, $m_{LL}$), wherein $m_{HH}$ is the slope of the fast Fourier transform of the system response measured during a pressure/frequency condition corresponding to a high pressure/high frequency condition, $m_{HL}$ is the slope of the fast Fourier transform of the system response measured during a pressure/frequency condition corresponding to a high pressure/low frequency condition, $m_{LH}$ is the slope of the fast Fourier transform of the system response measured during a pressure/frequency condition corresponding to a low pressure/high frequency condition, and $m_{LL}$ is the slope of the fast Fourier transform of the system response measured during a pressure/frequency condition corresponding to a low pressure/low frequency condition.

42. A control system for a failure mode testing system having a determinable system response, wherein the testing system includes a plurality of actuator cylinders, each cylinder operating at a pressure and a frequency, wherein the frequency of each of the cylinders is different, wherein the energy level and slope of the fast Fourier transform of the system response are capable of changing in response to pressure and frequency, comprising:

calculating the new target slope of the fast Fourier transform of the system response (S2) according to the following formula: $S2=S1+(S_{DESIRED}-S1)/n$, wherein S1 is the average slope of the fast Fourier transform of the system response, $S_{DESIRED}$ is the desired slope of the fast Fourier transform of the system response, and n is a number greater than 1.

43. A control system for a failure mode testing system having a determinable system response, wherein the testing system includes a plurality of actuator cylinders, each cylinder operating at a pressure and a frequency, wherein the frequency of each of the cylinders is different, wherein the energy level and slope of the fast Fourier transform of the system response are capable of changing in response to pressure and frequency, comprising:

calculating the new target pressure ($P_{NEW}$) according to the formula: $P_{NEW}=[(DsfE2-DsfE1-DefS2+DefS1-DepDsfP)/(DefDsp-DepDsf)]$, wherein Def is the change in energy due to frequency, Dep is the change in energy due to pressure, Dsf is the change in slope of the fast Fourier transform of the system response due to frequency, Dsp is the change in slope of the fast Fourier transform of the system response due to pressure, E1 is the average energy, E2 is the new target energy, S1 is the average slope of the fast Fourier transform of the system response, and S2 is the new target slope of the fast Fourier transform of the system response.

44. A control system for a failure mode testing system having a determinable system response, wherein the testing system includes a plurality of actuator cylinders, each cylinder operating at a pressure and a frequency, wherein the frequency of each of the cylinders is different, wherein the energy level and slope of the fast Fourier transform of the system response are capable of changing in response to pressure and frequency, comprising:

calculating the new target frequency ($F_{NEW}$) according to the formula: $F_{NEW}=[(DspE2-DspE1-DepS2+DepS1-DepDsfF)/(DefDsp-DepDsf)]$, wherein Def is the change in energy due to frequency, Dep is the change in energy due to pressure, Dsf is the change in slope of the fast Fourier transform of the system response due to frequency, Dsp is the change in slope of the fast Fourier transform of the system response due to pressure, E1 is the average energy, E2 is the new target energy, S1 is the average slope of the fast Fourier transform of the system response, and S2 is the new target slope of the fast Fourier transform of the system response.

45. A control system for a failure mode testing system having a plurality of actuator cylinders, each cylinder operating at an initial pressure and an initial frequency, wherein the frequency of each of the cylinders is different, comprising:

a pressure dither system, wherein the pressure of the actuator cylinder during extension and retraction is changed by an incremental amount of pressure (ditherp).

46. The control system in accordance with claim 45, wherein the dither pressure (ditherp) is calculated in accordance with the formula: $[((rnd)(maxdither))-((rnd)(maxdither2))]$, wherein rnd is a random number function between 0 and 1, and maxdither is the pre-selected maximum pressure difference for dither pressure (ditherp).

47. A control system for a failure mode testing system having a plurality of actuator cylinders, each cylinder operating at an initial pressure and an initial frequency, wherein the frequency of each of the cylinders is different, comprising:

a frequency ringing system, wherein the location of a particular frequency is randomly reordered among the plurality of actuator cylinders.

48. The control system in accordance with claim 47, wherein the frequency ringing system is calculated in accordance with the formula: cylinder $i=Mode(i+Mode(C1,6),6)+1$, wherein i is the cylinder number, Mode is the remainder of the quotient between any two given numbers, and C1 is the count number representing a status change in the cylinder frequency location.

49. A control system for a failure mode testing system having a determinable system response, wherein the testing system includes a plurality of actuator cylinders, each cylinder operating at an initial pressure and an initial frequency, wherein the frequency of each of the cylinders is different, comprising:

a) selecting a desired system response;

b) changing an operational parameter of the cylinders by a pre-selected amount in order to create a first pressure/frequency condition, wherein the operational parameter is selected from the group consisting of pressure, frequency, and combinations thereof; and c) determining the system response under the first pressure/frequency condition.

50. The control system in accordance with claim 49, further comprising:

d) storing the system response determination of the first pressure/frequency condition in a data storage medium.

51. The control system in accordance with claim 50, further comprising:

e) changing an operational parameter of the cylinders by a pre-selected amount in order to create a second pressure/frequency condition different from the first pressure/frequency condition; and f) determining the system response under the second pressure/frequency condition.

52. The control system in accordance with claim 51, further comprising:

g) storing the system response determination of the second pressure/frequency condition in a data storage medium.

53. The control system in accordance with claim 52, further comprising:

h) changing an operational parameter of the cylinders by a pre-selected amount in order to create a third pressure/frequency condition different from the first and second pressure/frequency conditions; and i) determining the system response under the third pressure/frequency condition.

54. The control system in accordance with claim 53, further comprising:

j) storing the system response determination of the third pressure/frequency condition in a data storage medium.

55. The control system in accordance with claim 54, further comprising:

k) changing an operational parameter of the cylinders by a pre-selected amount in order to create a fourth pressure/frequency condition different from the first, second, and third pressure/frequency conditions; and l) determining the system response under the fourth pressure/frequency condition.

56. The control system in accordance with claim 55, further comprising:

m) storing the system response determination of the fourth pressure/frequency condition in a data storage medium.

57. The control system in accordance with claim 56, further comprising:

n) determining whether the desired system response is present.

58. The control system in accordance with claim 57, further comprising:

o) decreasing the pre-selected amount that the operational parameter is changed by and repeating steps b) through n), until the desired system response is present.

59. The control system in accordance with claim 57, further comprising:

p) increasing the pre-selected amount that the operational parameter is increased by and repeating steps b) through n), until the desired system response is present.

60. The control system in accordance with claim 49, further comprising:

a pressure dither system, wherein the pressure of the actuator cylinder during extension and retraction is changed by an incremental amount of pressure (ditherp).

61. The control system in accordance with claim 60, wherein the dither pressure (ditherp) is calculated in accordance with the formula: [((rnd)(maxdither))−((rnd)(maxdither2))], wherein rnd is a random number function between 0 and 1, and maxdither is the pre-selected maximum pressure difference for dither pressure (ditherp).

62. The control system in accordance with claim 49, further comprising:

a frequency ringing system, wherein the location of a particular frequency is reordered among the plurality of actuator cylinders.

63. The control system in accordance with claim 62, wherein the frequency ringing system is calculated in accordance with the formula: cylinder i=Mode(i+Mode(C1, 6),6)+1, wherein i is the cylinder number, Mode is the remainder of the quotient between any two given numbers, and C1 is the count number representing a status change in the cylinder frequency location.

64. A control system for a failure mode testing system having a determinable system response, wherein the testing system includes a plurality of actuator cylinders, each cylinder operating at an initial pressure and an initial frequency, wherein the frequency of each of the cylinders is different, comprising:

a) selecting a desired system response;

b) determining the system response;

c) determining whether the desired system response is present; and d) changing an operational parameter of the cylinders by a sufficient amount in order to achieve the desired system response, wherein the operational parameter is selected from the group consisting of pressure, frequency, and combinations thereof.

65. The control system in accordance with claim 64, further comprising:

e) decreasing the amount that the operational parameter is changed by and repeating steps b) through c), until the desired system response is present.

66. The control system in accordance with claim 64, further comprising:

f) increasing the amount that the operational parameter is increased by and repeating steps b) through c) until the desired system response is present.

67. The control system in accordance with claim 64, further comprising:

a pressure dither system, wherein the pressure of the actuator cylinder during extension and retraction is changed by an incremental amount of pressure (ditherp).

68. The control system in accordance with claim 64, wherein the dither pressure (ditherp) is calculated in accordance with the formula: [((rnd)(maxdither))−((rnd)(maxdither2))], wherein rnd is a random number function between 0 and 1, and maxdither is the pre-selected maximum pressure difference for dither pressure (ditherp).

69. The control system in accordance with claim 64, further comprising:

a frequency ringing system, wherein the location of a particular frequency is reordered among the plurality of actuator cylinders.

70. The control system in accordance with claim 69, wherein the frequency ringing system is calculated in accordance with the formula: cylinder i=Mode(i+Mode(C1, 6),6)+1, wherein i is the cylinder number, Mode is the remainder of the quotient between any two given numbers, and C1 is the count number representing a status change in the cylinder frequency location.

* * * * *